US011364345B2

(12) United States Patent
Soares et al.

(10) Patent No.: US 11,364,345 B2
(45) Date of Patent: Jun. 21, 2022

(54) MEDICAMENT INJECTOR DEVICE

(71) Applicant: SANOFI, Paris (FR)

(72) Inventors: Francisco Soares, Frankfurt am Main (DE); Bernhard Forys, Frankfurt am Main (DE); Stefan Verlaak, Paderno d'Adda (IT); Ilario Melzi, Milan (IT)

(73) Assignee: Sanofi, Paris (FR)

( * ) Notice: Subject to any disclaimer, the term of this patent is extended or adjusted under 35 U.S.C. 154(b) by 567 days.

(21) Appl. No.: 16/318,024

(22) PCT Filed: Jul. 12, 2017

(86) PCT No.: PCT/EP2017/067514
§ 371 (c)(1),
(2) Date: Jan. 15, 2019

(87) PCT Pub. No.: WO2018/015238
PCT Pub. Date: Jan. 25, 2018

(65) Prior Publication Data
US 2021/0260295 A1     Aug. 26, 2021

(30) Foreign Application Priority Data

Jul. 19, 2016  (EP) .................................. 16305928

(51) Int. Cl.
*A61M 5/24* (2006.01)
*A61M 5/32* (2006.01)
(52) U.S. Cl.
CPC .......... *A61M 5/2466* (2013.01); *A61M 5/326* (2013.01); *A61M 2005/247* (2013.01)
(58) Field of Classification Search
CPC .......... A61M 2005/247; A61M 5/2466; A61M 2005/2474; A61M 2005/206
See application file for complete search history.

(56) References Cited

U.S. PATENT DOCUMENTS 3,605,744 A *  9/1971  Dwyer ................ A61M 5/2033
                                                604/506
5,658,259 A *  8/1997  Pearson ............... A61M 5/2033
                                                604/136
(Continued)

FOREIGN PATENT DOCUMENTS

CN         101903057        12/2010
CN         101977645         2/2011
(Continued)

OTHER PUBLICATIONS

International Preliminary Report on Patentability in Application No. PCT/EP2017/067514, dated Jan. 22, 2019, 7 pages.
(Continued)

*Primary Examiner* — Emily L Schmidt
(74) *Attorney, Agent, or Firm* — Fish & Richardson P.C.

(57) ABSTRACT

An injector device for delivering a liquid medicament comprises an injector body having a proximal end and a distal end. The injector device further includes a syringe slidably received in the injector body and moveable from a first position to a second position towards the distal end of the body. Additionally, the injector device comprises a needle holder between the syringe and the distal end of the body, and a needle held in the needle holder. The needle has a distal end extending toward an opening in the distal end of the body, and a proximal end extending toward the syringe. The injector device also comprises a syringe biasing member within the body configured to bias the syringe into the second position. The syringe is spaced from the needle in the first position and is in engagement with the proximal end of the needle in the second position.

18 Claims, 4 Drawing Sheets

(56) References Cited

U.S. PATENT DOCUMENTS

| | | | |
|---|---|---|---|
| 2007/0073232 A1 | 3/2007 | Pickhard | |
| 2008/0009807 A1 | 1/2008 | Hommann | |
| 2011/0004165 A1 | 1/2011 | Iio et al. | |
| 2016/0144131 A1 | 5/2016 | Schwirtz et al. | |
| 2017/0143902 A1* | 5/2017 | Hansen | A61M 5/3245 |

FOREIGN PATENT DOCUMENTS

| | | |
|---|---|---|
| CN | 101983079 | 3/2011 |
| JP | 2007-503853 | 3/2007 |
| JP | 2013-508054 | 3/2013 |
| JP | 2013-534164 | 9/2013 |
| JP | 2016-524930 | 8/2016 |
| WO | WO 2005/021070 | 3/2005 |
| WO | WO 2009/037141 | 3/2009 |
| WO | WO 2009/063030 | 5/2009 |
| WO | WO 2011/048422 | 4/2011 |
| WO | WO 2012/022810 | 2/2012 |
| WO | WO 2014/095424 | 6/2014 |
| WO | WO 2016/075254 | 5/2016 |

OTHER PUBLICATIONS

International Search Report and Written Opinion in Application No. PCT/EP2017/067514, dated Oct. 5, 2017, 9 pages.

* cited by examiner

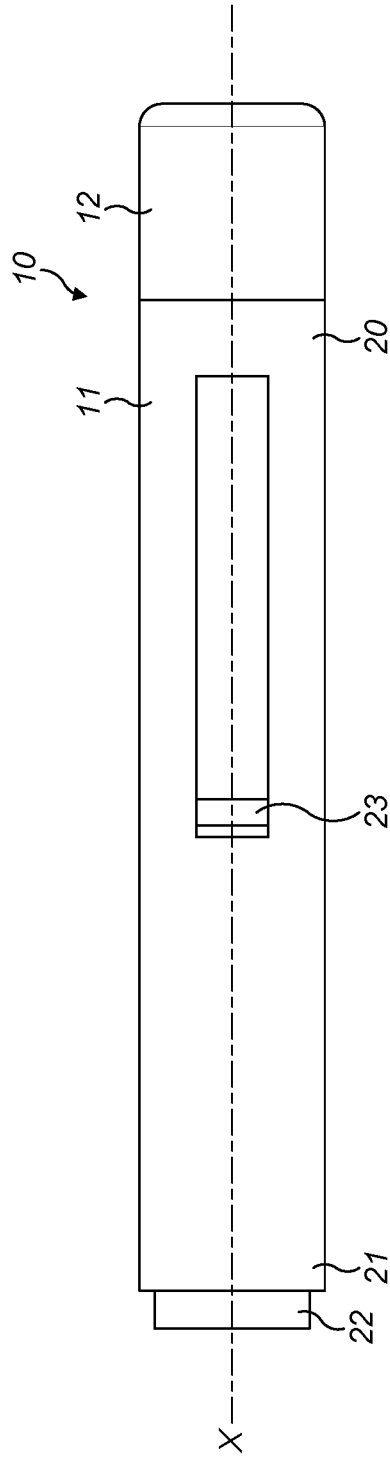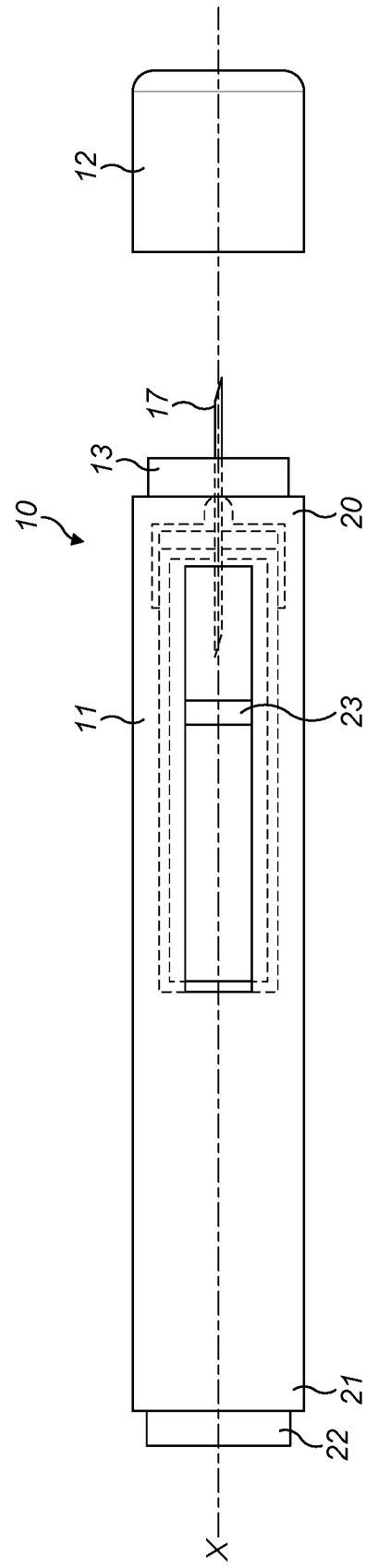

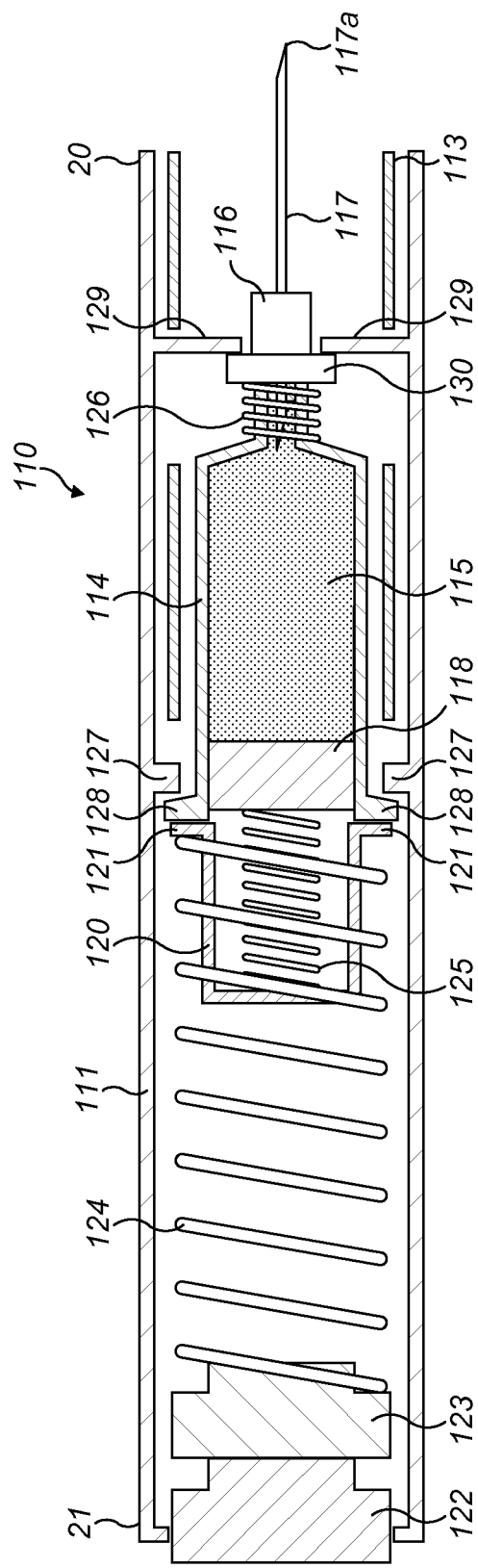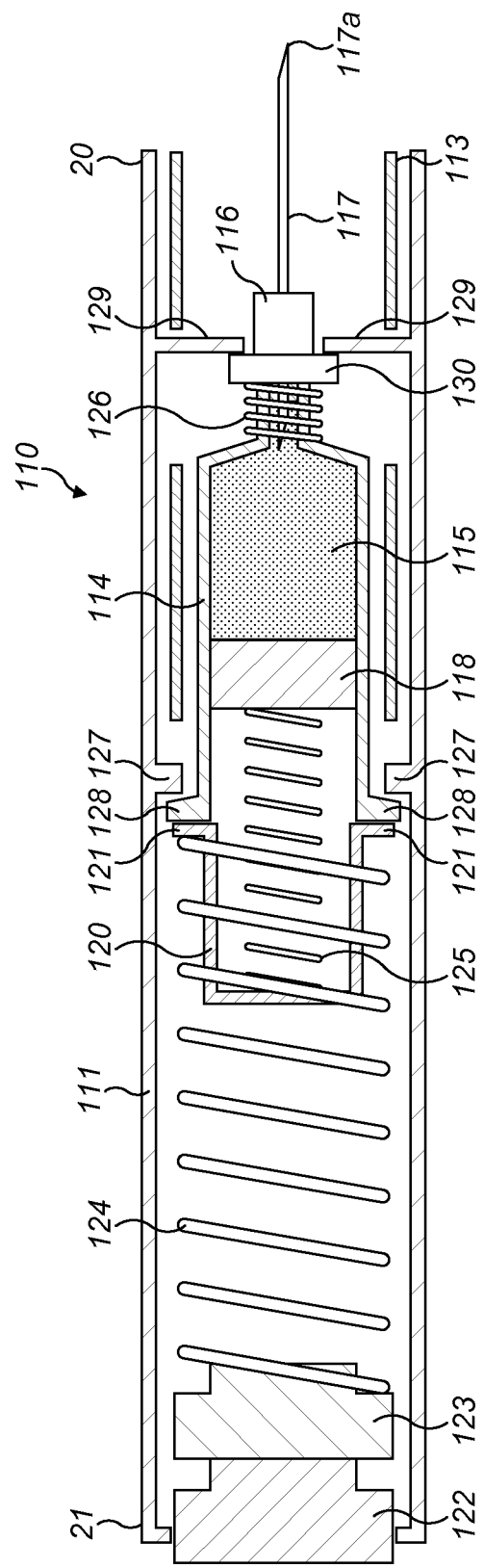

MEDICAMENT INJECTOR DEVICE

CROSS REFERENCE TO RELATED APPLICATIONS

The present application is the national stage entry of International Patent Application No. PCT/EP2017/067514, filed on Jul. 12, 2017, and claims priority to Application No. EP 16305928.0, filed on Jul. 19, 2016, the disclosures of which are incorporated herein by reference.

TECHNICAL FIELD

This disclosure relates to an injector device for delivery of a liquid medicament.

BACKGROUND

Injector devices are used to deliver a range of liquid medicaments. These devices have application where regular injections by persons without formal medical training occur. This is common among patients where self-treatment enables effective management of their disease.

SUMMARY

According to the disclosure there is provided an injector device for delivering a liquid medicament, comprising an injector body having a proximal end and a distal end, a syringe slidably received in the injector body and moveable from a first position to a second position towards the distal end of the body, a needle holder between the syringe and the distal end of the body, a needle held in the needle holder and including a distal end extending toward an opening in the distal end of the body, and a proximal end extending toward the syringe, and a syringe biasing member within the body configured to bias the syringe into the second position, wherein the syringe is spaced from the needle in the first position and is in engagement with the proximal end of the needle in the second position and wherein the needle holder is slidably mounted in the body and moveable from a retracted position to an extended position toward the distal end of the body.

The syringe may include a distal end with an opening sealed with a septum, and the injector device may be configured such that the proximal end of the needle pierces the septum when the syringe moves into the second position. This may advantageously help towards providing the advantage of maintaining a sealed medicament container until injection is to be commenced, and provide ease of use of the injector device by a user.

The needle holder being slidably mounted in the body and moveable from a retracted position to an extended position toward the distal end of the body may advantageously help towards providing the advantage of effectively engaging the syringe with the needle.

The body may include a needle holder stop against which the needle holder abuts in the extended position. This may advantageously help towards providing the advantage of retaining the needle in correct location, and also while being engaged by the syringe.

The body may include a syringe stop against which the needle holder abuts in the second position. This may advantageously help towards providing the advantage of retaining the syringe in the correct final position.

The injector device may further comprise a needle holder biasing member configured to bias the needle holder into the extended position. This may advantageously help towards providing the advantage of assisting the needle holder to move into an operative position.

The syringe biasing member may be configured to exert a greater biasing force than the needle holder biasing member. This may advantageously help towards providing the advantage of ensuring the needle fully engages with the syringe.

The syringe may include a stopper, which is slidable within the syringe towards a distal end thereof to expel medicament therefrom, and the injector device may further comprise a stopper biasing member configured to bias the stopper towards the distal end of the syringe. This may advantageously help towards providing the advantage of effectively delivering medicament from the syringe upon actuation of the device.

The syringe biasing member and the stopper biasing member may be coil springs and the stopper biasing member maybe is concentric with, and at least partially received within, the syringe biasing member. This may advantageously help towards providing the advantage of providing a compact and space-efficient device configuration.

The injector device may further comprise a release mechanism configured to retain the stopper against the force of the stopper biasing member and operable to release the stopper to allow movement within the syringe under the biasing force of the stopper biasing member. This may advantageously help towards providing the advantage of allowing user-control of when an injection process is to be initiated.

The injector device may further comprise a syringe ram in abutment with the syringe and disposed towards the proximal end of the body from the syringe, and the syringe biasing member may act on the syringe ram to exert a biasing force on the syringe. This may advantageously help towards providing the advantage of effectively engaging the syringe to move the syringe from the first to the second position.

The syringe ram may include a hollow section and the stopper biasing member may be at least partially received within the hollow section of the syringe ram. This may advantageously help towards providing the advantage of a compact and space-efficient device configuration.

The injector device may further comprise an actuation mechanism configured to retain the syringe in the first position until the actuation mechanism is activated and the syringe is thereby released. The actuation mechanism may include an actuation button to activate the actuation mechanism. This may advantageously help towards providing the advantage of user-control of the injection process.

The injector device may further comprise a needle sleeve moveable between an extended position in which the needle sleeve extends from the distal end of the injector body and surrounds the needle, and a retracted position in which the needle sleeve is retracted into the injector body to expose the needle. This may advantageously help towards providing the advantage of avoiding needle injury before and after use of the device.

The syringe may contain a liquid medicament or a cartridge of liquid medicament.

The present disclosure also provides a method of operation of an injector device for delivering a liquid medicament comprising an injector body having a proximal end and a distal end, a syringe slidably received in the injector body, a needle holder between the syringe and the distal end of the body, the needle holder slidably mounted in the body and moveable from a retracted position to an extended position toward the distal end of the body, a needle held in the needle holder and including a distal end extending toward an opening in the distal end of the body, and a proximal end extending toward the syringe, and a syringe biasing member within the body, the method comprising moving the syringe from a first position in which the syringe is spaced from the needle into a second position towards the distal end of the body under the biasing force of the syringe biasing member, and the syringe engaging with the proximal end of the needle in the second position.

Some embodiments advantageously make the medicament delivery process straight-forward and intuitive for the patient to complete themselves. This can reduce the likelihood of improper use and thus reduce ineffective treatment of the medical condition and potential injury or discomfort to the patient.

BRIEF DESCRIPTION OF THE FIGURES

So that the present invention may be more fully understood, embodiments thereof will now be described with reference to the accompanying drawings in which:

FIG. 1A shows an injector device with a cap attached;

FIG. 1B shows the injector device of FIG. 1A with the cap removed;

FIG. 4 shows the injector device of FIG. 2 in a second intermediate configuration during use;

FIG. 5 shows the injector device of FIG. 2 in a third intermediate configuration during use.

DETAILED DESCRIPTION

Figure 2:
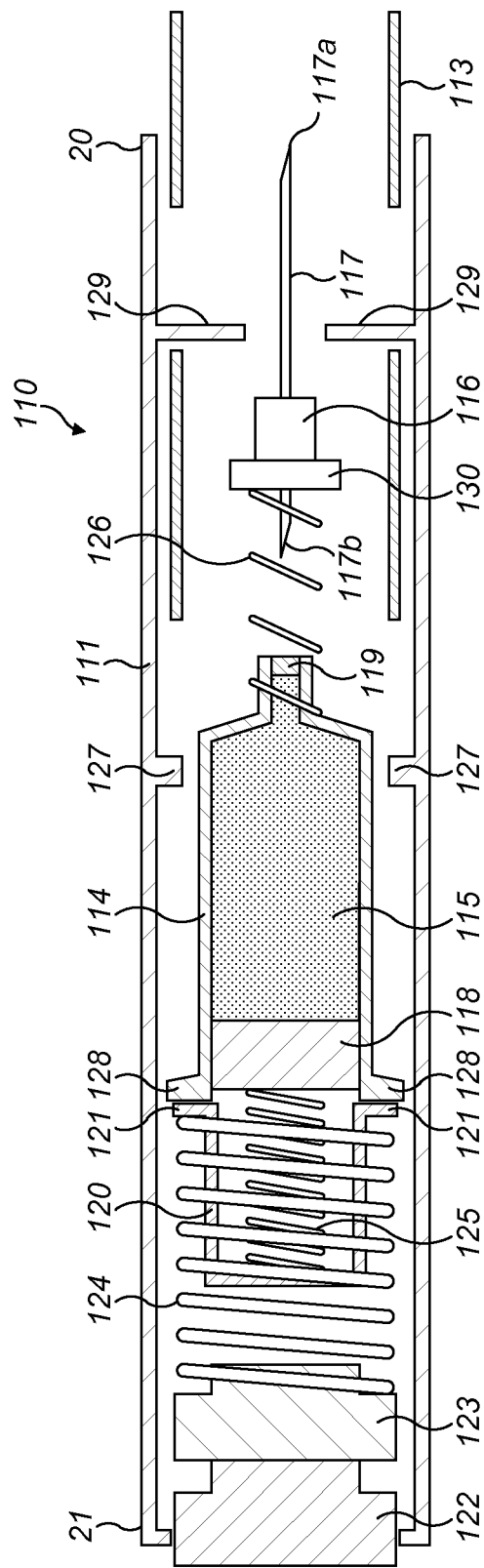
FIG. 2 shows a schematic view of an injector device according to a first embodiment in a start configuration.

A drug delivery device, as described herein, may be configured to inject a medicament into a patient. For example, delivery could be sub-cutaneous, intra-muscular, or intravenous. Such a device could be operated by a patient or care-giver, such as a nurse or physician, and can include various types of safety syringe, pen-injector, or auto-injector. The device can include a cartridge-based system that requires piercing a sealed ampule before use. Volumes of medicament delivered with these various devices can range from about 0.5 ml to about 2 ml. Yet another device can include a large volume device ("LVD") or patch pump, configured to adhere to a patient's skin for a period of time (e.g., about 5, 15, 30, 60, or 120 minutes) to deliver a "large" volume of medicament (typically about 2 ml to about 10 ml).

In combination with a specific medicament, the presently described devices may also be customized in order to operate within required specifications. For example, the device may be customized to inject a medicament within a certain time period (e.g., about 3 to about 20 seconds for auto-injectors, and about 10 minutes to about 60 minutes for an LVD). Other specifications can include a low or minimal level of discomfort, or to certain conditions related to human factors, shelf-life, expiry, biocompatibility, environmental considerations, etc. Such variations can arise due to various factors, such as, for example, a drug ranging in viscosity from about 3 cP to about 50 cP. Consequently, a drug delivery device will often include a hollow needle ranging from about 25 to about 31 Gauge in size. Common sizes are 27 and 29 Gauge.

The delivery devices described herein can also include one or more automated functions. For example, one or more of needle insertion, medicament injection, and needle retraction can be automated. Energy for one or more automation steps can be provided by one or more energy sources. Energy sources can include, for example, mechanical, pneumatic, chemical, or electrical energy. For example, mechanical energy sources can include springs, levers, elastomers, or other mechanical mechanisms to store or release energy. One or more energy sources can be combined into a single device. Devices can further include gears, valves, or other mechanisms to convert energy into movement of one or more components of a device.

The one or more automated functions of an auto-injector may each be activated via an activation mechanism. Such an activation mechanism can include one or more of a button, a lever, a needle sleeve, or other activation component. Activation of an automated function may be a one-step or multi-step process. That is, a user may need to activate one or more activation components in order to cause the automated function. For example, in a one-step process, a user may depress a needle sleeve against their body in order to cause injection of a medicament. Other devices may require a multi-step activation of an automated function. For example, a user may be required to depress a button and retract a needle shield in order to cause injection.

In addition, activation of one automated function may activate one or more subsequent automated functions, thereby forming an activation sequence. For example, activation of a first automated function may activate at least two of needle insertion, medicament injection, and needle retraction. Some devices may also require a specific sequence of steps to cause the one or more automated functions to occur. Other devices may operate with a sequence of independent steps.

Some delivery devices can include one or more functions of a safety syringe, pen-injector, or auto-injector. For example, a delivery device could include a mechanical energy source configured to automatically inject a medicament (as typically found in an auto-injector) and a dose setting mechanism (as typically found in a pen-injector).

According to some embodiments of the present disclosure, an exemplary drug delivery device 10 is shown in FIGS. 1A & 1B. The device 10, as described above, is configured to inject a medicament into a patient's body. The device 10 includes a housing 11 which typically contains a reservoir containing the medicament to be injected (e.g., a syringe) and the components required to facilitate one or more steps of the delivery process. The device 10 can also include a cap assembly 12 that can be detachably mounted to the housing 11. Typically, a user must remove the cap 12 from the housing 11 before the device 10 can be operated.

As shown, the housing 11 is substantially cylindrical and has a substantially constant diameter along the longitudinal axis X. The housing 11 has a distal region 20 and a proximal region 21. The term "distal" refers to a location that is relatively closer to a site of injection, and the term "proximal" refers to a location that is relatively further away from the injection site.

The device 10 can also include a needle sleeve 13 coupled to the housing 11 to permit movement of the sleeve 13 relative to the housing 11. For example, the sleeve 13 can move in a longitudinal direction parallel to longitudinal axis X. Specifically, movement of the sleeve 13 in a proximal direction can permit a needle 17 to extend from the distal region 20 of the housing 11.

Insertion of the needle 17 can occur via several mechanisms. For example, the needle 17 may be fixedly located relative to the housing 11 and initially be located within an extended needle the sleeve 13. Proximal movement of the sleeve 13 by placing a distal end of the sleeve 13 against a patient's body and moving the housing 11 in a distal direction will uncover distal end of the needle 17. Such relative movement allows the distal end of the needle 17 to extend into the patient's body. Such insertion is termed "manual" insertion as the needle 17 is manually inserted via the patient's manual movement of the housing 11 relative to the sleeve 13.

Another form of insertion is "automated," whereby the needle 17 moves relative to the housing 11. Such insertion can be triggered by movement of the sleeve 13 or by another form of activation, such as, for example, a button 22. As shown in FIGS. 1A & 1B, the button 22 is located at a proximal end of the housing 11. However, in other embodiments, the button 22 could be located on a side of the housing 11.

Other manual or automated features can include drug injection or needle retraction, or both. Injection is the process by which a bung or piston 23 is moved from a proximal location within a syringe (not shown in FIGS. 1A and 1B) to a more distal location within the syringe in order to force a medicament from the syringe through the needle 17. In some embodiments, a drive spring (not shown in FIGS. 1A and 1B) is under compression before the device 10 is activated. A proximal end of the drive spring can be fixed within proximal region 21 of the housing 11, and a distal end of the drive spring can be configured to apply a compressive force to a proximal surface of the piston 23. Following activation, at least part of the energy stored in the drive spring can be applied to the proximal surface of the piston 23. This compressive force can act on the piston 23 to move it in a distal direction. Such distal movement acts to compress the liquid medicament within the syringe, forcing it out of the needle 17.

Following injection, the needle 17 can be retracted within the sleeve 13 or the housing 11. Retraction can occur when the sleeve 13 moves distally as a user removes the device 10 from a patient's body. This can occur as the needle 17 remains fixedly located relative to the housing 11. Once a distal end of the sleeve 13 has moved past a distal end of the needle 17, and the needle 17 is covered, the sleeve 13 can be locked. Such locking can include locking any proximal movement of the sleeve 13 relative to the housing 11.

Another form of needle retraction can occur if the needle 17 is moved relative to the housing 11. Such movement can occur if the syringe within the housing 11 is moved in a proximal direction relative to the housing 11. This proximal movement can be achieved by using a retraction spring (not shown), located in distal region 20. A compressed retraction spring, when activated, can supply sufficient force to the syringe to move it in a proximal direction. Following sufficient retraction, any relative movement between the needle 17 and the housing 11 can be locked with a locking mechanism. In addition, the button 22 or other components of the device 10 can be locked as required.

Referring now to FIGS. 2 to 6, an injector device 110 according to an embodiment is schematically shown comprising an injector housing body 111 (hereafter "body") having a distal region 20 and a proximal region 21. The body 111 may include a needle sleeve 113 extending therefrom and which is retractable into the body 111 and may be biased in a direction to extend from the body 111.

Figure 3:
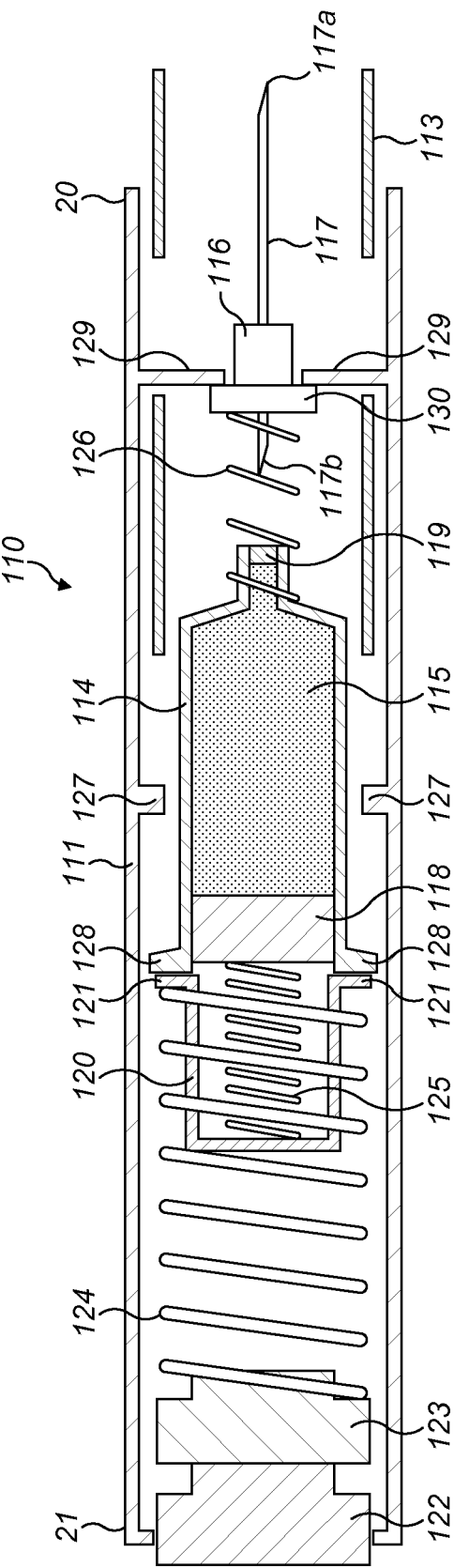
FIG. 3 shows the injector device of FIG. 2 in a first intermediate configuration during use.

The body 111 comprises a syringe holder portion configured to receive a syringe 114 or cartridge of liquid medicament 115. Alternatively, the syringe 114 may be configured to receive a cartridge of liquid medicament 115. The syringe 114 is slidably mounted within the body 111 and is moveable between a pre-use position (shown in FIG. 2) to a use position (shown in FIGS. 4 to 6). FIG. 3 shows the syringe 114 in an intermediate position between the pre-use position and the use position.

A needle 117 is held in a needle holder 116 located towards a distal end of the body 111 from the syringe 114. The needle 117 includes a distal end 117a nearer the distal end 20 of the body 111 and a proximal end 117b nearer the proximal end 21 of the body 111. The needle holder 116 is slidably mounted within the body 111 and is moveable between a retracted position (shown in FIG. 2) and an extended position (shown in FIGS. 3 to 6). In the extended position of the needle holder 116, the needle 117 extends beyond the distal end 20 of the body 111. The needle sleeve 113 surrounds the needle 117 in its extended position and the needle 117 is exposed when the needle sleeve 113 is moved to its retracted position.

The syringe 114 includes a stopper 118 at an opposite end to the needle 117 which seals against an inside wall of the syringe 114 to retain the liquid medicament 115 inside the syringe 114. The opposite end of the syringe 114, proximate the needle holder 116, includes an opening with a septum 119 therein, which seals the opening.

A cylindrical syringe ram 120 is provided at the proximal end of the syringe 114 that is the end of the syringe 114 nearest the proximal end 21 of the body 111. The syringe ram 120 includes a peripheral flange 121, which abuts against the proximal end of the syringe 114.

An actuation mechanism 123 (only shown schematically) is provided at the within the body at the proximal end 21 thereof. A button 122 is located at a proximal end 21 of body 111 and is operable to activate the actuation mechanism 123. The actuation mechanism may comprise a variety of mechanisms within the scope, including a powered automated device, and may include control or monitoring electronics to control/monitor the operation of the injector device 110. The actuation mechanism may comprise a power pack to drive the syringe ram 120. A plunger (not shown) may be provided to drive the syringe ram 120. Alternatively, the actuation mechanism may be purely mechanical without being powered. The actuation mechanism may include a releasable locking mechanism configured to engage the syringe ram 120. The locking mechanism may be configured to disengage from the syringe ram 120 when the button 122 is depressed.

A syringe spring 124 is disposed between the actuation mechanism 123 and the syringe ram 120. The syringe spring 124 is a compression spring and is in a compressed state when the syringe is in the pre-use position shown in FIG. 2. The syringe spring 124 is disposed over the syringe ram 120 and seats against the peripheral flange 121. The syringe spring 124 and syringe ram 120 thereby act to bias the syringe 114 towards the use position.

A stopper spring 125 is provided within the cylindrical portion of the syringe ram 120. One end of the stopper spring 125 abuts against the inside of the end wall of the syringe ram 120. The other end of the stopper spring 125 abuts against the stopper 118. The stopper spring 125 is a compression spring and is in a compressed state when the syringe 114 is in the pre-use position and while liquid medicament 115 is within the syringe 114. The stopper spring 125 acts to bias the stopper 118 in a direction towards the distal end 20 of the syringe 114 to expel medicament from the syringe 114. The stopper 118 is prevented from moving under the force of the stopper spring 125 while the septum seals the opening in the distal end of the syringe 114.

Figure 6:
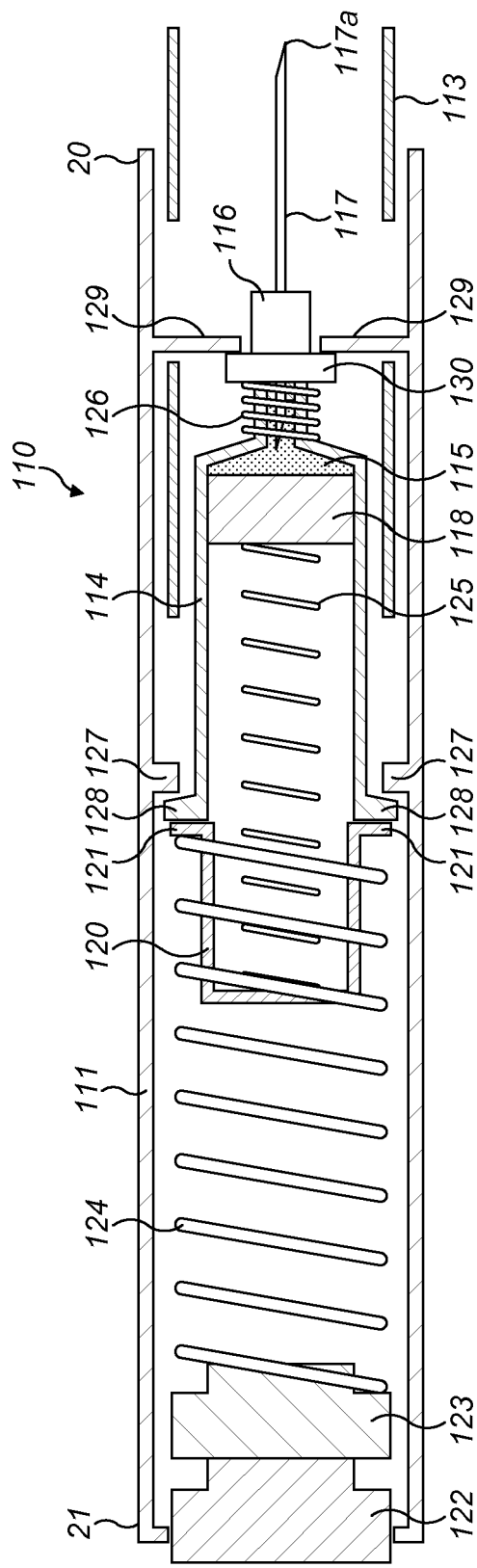
FIG. 6 shows the injector device of FIG. 2 in a finish configuration.

A needle holder spring 126 is provided between the needle holder 116 and the distal end of the syringe 114. The needle holder spring 126 is a compression spring. The needle holder spring 126 is in an expanded state when the syringe 114 and needle holder 116 are spaced apart (as shown in FIGS. 2 and 3). The needle holder spring 126 is in a compressed state when the syringe 114 and needle holder 116 are in abutment (as shown in FIGS. 4 to 6). The needle holder spring 126 thereby serves to bias the needle holder 116 away from the syringe 114.

The body 111 includes syringe stops 127, which abut against a projecting portion 128 of the syringe 114 when the syringe 114 reaches the use position. The syringe stops 127 prevent further movement of the syringe 114 towards the distal end 20 of the body 111. The syringe stops 127 retain the syringe 114 in the use position against the force of the syringe spring 124.

The body 111 includes needle holder stops 129, which abut against a projecting portion 130 of the needle holder 116 when the needle holder 116 reaches the extended position. The needle holder stops 129 prevent further movement of the needle holder 116 towards the distal end 20 of the body 111. The needle holder stops 129 retain the needle holder 116 in the extended position against the force of the needle holder spring 126.

Operation of the injector device 110 of the exemplary embodiment will now be described. The injector device 110 is initially in the start configuration shown in FIG. 2. In the start configuration, the needle sleeve 113 is in the extended position, the syringe 114 is in the pre-use position and the needle holder 116 is in the retracted position.

The distal end 20 of the injector device 110 is pressed against the injection site on a patient's body. The needle sleeve 113 slides from the extended position to the retracted position inside the body 111. In the embodiment shown in the Figures, the distal end 117a of the needle 117 does not extend beyond the distal end 20 of the body 111 when the needle holder 116 is in the retracted position. As such, the distal end 117a of the needle 117 would not pierce the patient's skin at this stage of the operation. However, in an alternative embodiment, the distal end 117a of the needle 117 may extend beyond the distal end 20 of the body 111 in both the extended and retracted positions of the needle holder 116. In such an alternative embodiment, only the needle sleeve 113 may conceal the distal end 117a of the needle 117 when the needle sleeve 113 is in the extended position. In such an alternative embodiment, pressing the injector device 110 against the injection site and causing the needle sleeve 113 to retract into the body 111 may expose the distal end 117a of the needle 117 so that it pierces the patient's skin whilst the needle holder 116 is still in the retracted position.

The button 122 is then pushed to activate the actuation mechanism 123. This releases the syringe ram 120. The syringe ram 120 pushes the syringe 114 towards the distal end 20 of the body 111 under the force of the syringe spring 124. As the syringe 114 slides towards the distal end 20 of the body 111, the needle holder spring 126 pushes the needle holder 116 in a direction towards the distal end 20 of the body 111. The syringe 114 and needle holder 116 thereby slide together in a direction towards the distal end 20 of the body 111.

The syringe 114 and needle holder 116 slide together in a direction towards the distal end 20 of the body 111 until the needle holder 116 abuts the needle holder stops 129. The needle holder 116 is thereby in the extended position. This is shown as the first intermediate configuration of FIG. 3. (Note however, that the needle sleeve 113 is shown in its extended state in FIG. 3. It will be appreciated that when pressed against the injection site, the needle sleeve 113 would be in its retracted position and the distal end 117a of the needle 117 would be exposed). This movement of the needle holder 116 into the extended position causes the needle 117 to pierce the patient's skin at the injection site. In the alternative embodiment described above, however, in which the distal end 117a of the needle 117 extends beyond the distal end 20 of the body 111 even when the needle holder 116 is in the retracted position, the needle 117 would already have pierced the patient's skin when the injector device 110 was pressed against the injection site. Therefore, movement of the needle holder 116 into the extended position would cause the needle 117 to extend further into the patient's skin.

From the first intermediate position, the syringe 114 continues to slides towards the distal end 20 of the body 111 under the force of the syringe spring 124. However, since the needle holder 116 is abutting the needle holder stops 129, the syringe 114 moves towards the needle holder 116, compressing the needle holder spring 126. It will be appreciated therefore that the syringe spring 124 is configured to exert a stronger force than the needle holder spring 126. The syringe 114 continues to slide towards the needle holder 116 until it abuts the syringe stops 127 in the use position. At this position, the distal end of the syringe 114 also abuts the needle holder 116. This causes the proximal end 117b of the needle 117 to piece the septum 119 and render the needle 117 in fluid communication with the reservoir of liquid medicament 115 within the syringe 114. The injector device 110 is then in the second intermediate configuration shown in FIG. 4. Note that the needle sleeve 113 is shown in the retracted position in FIG. 4 and the distal end 117a of the needle 117 is exposed.

With the septum pierced by the needle 117, and the needle 117 piercing the patient's skin, the medicament 115 is able to be delivered to the injection site. The stopper spring 125 forces the stopper 118 in a direction towards the distal end 20 of the body 111, which expels the medicament 115 from the syringe 114 and into the patient. Half way through the medicament delivery process, the stopper 118 is part-way along the length of the syringe 114, as shown in the third intermediate configuration of FIG. 5.

The stopper 118 continues to move towards the distal end 20 of the body 111 under the force of the stopper spring 125, until the stopper 118 reaches the distal end of the syringe 114. At this point, the liquid medicament 115 has been fully expelled from the syringe 114. The injector device 110 is then in the finish configuration shown in FIG. 6. Once the injector device 110 has reached the finish configuration, the injector device 110 can be removed from the patient's body. The needle sleeve 113 may then move to the extended position under suitable biasing means (not shown) to conceal the distal end 117a of the needle 117, to avoid accidental injury. This configuration with the needle sleeve 113 in the extended position is shown in FIG. 6. The injector device 110 may include an automatic locking mechanism the locks the needle sleeve 113 in the extended position once the injector device has been used. Such locking mechanism may be mechanically or electronically linked to the syringe being disposed in the use position and/or to the needle holder 116 being disposed in the extended position.

In an alternative embodiment, the stopper spring 125, and/or the stopper 118, may include a release mechanism with a release actuator. This may enable a user to separately control when a medicament 115 delivery process commences, independently of the syringe 114 movement to the use position and of the needle holder 116 movement to the extended position.

It is intended within the scope that the needle holder 116 may alternatively be fixed relative to the body 111. In such an embodiment, the syringe 114 would be moveable within the body 111 and would slide from the pre-use position to the use position, in which the proximal end 117b of the needle 117 pierces the septum 119. In such an embodiment, the needle sleeve 113 may preferable conceal the distal end 117a of the needle 117 when the needle sleeve 113 is in the extended position.

The body 111 may include one or more guide elements to guide sliding movement of the syringe 114 within the body 111. Such guide elements may include one or more cooperating projections and recesses to receive the projections, formed in one of the syringe 114 and/or body 111 respectively.

Similarly, the body 111 may include one or more guide elements to guide sliding movement of the needle holder 116 within the body 111. Such guide elements may include one or more cooperating projections and recesses to receive the projections, formed in one of the needle holder 116 and/or body 111 respectively.

The terms "drug" or "medicament" are used herein to describe one or more pharmaceutically active compounds. As described below, a drug or medicament can include at least one small or large molecule, or combinations thereof, in various types of formulations, for the treatment of one or more diseases. Exemplary pharmaceutically active compounds may include small molecules; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more of these drugs are also contemplated.

The term "drug delivery device" shall encompass any type of device or system configured to dispense a drug into a human or animal body. Without limitation, a drug delivery device may be an injection device (e.g., syringe, pen injector, auto injector, large-volume device, pump, perfusion system, or other device configured for intraocular, subcutaneous, intramuscular, or intravascular delivery), skin patch (e.g., osmotic, chemical, micro-needle), inhaler (e.g., nasal or pulmonary), implantable (e.g., coated stent, capsule), or feeding systems for the gastro-intestinal tract. The presently described drugs may be particularly useful with injection devices that include a needle, e.g., a small gauge needle.

The drug or medicament may be contained in a primary package or "drug container" adapted for use with a drug delivery device. The drug container may be, e.g., a cartridge, syringe, reservoir, or other vessel configured to provide a suitable chamber for storage (e.g., short- or long-term storage) of one or more pharmaceutically active compounds. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of a drug formulation (e.g., a drug and a diluent, or two different types of drugs) separately, one in each chamber. In such instances, the two chambers of the dual-chamber cartridge may be configured to allow mixing between the two or more components of the drug or medicament prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drug delivery devices and drugs described herein can be used for the treatment and/or prophylaxis of many different types of disorders. Exemplary disorders include, e.g., diabetes mellitus or complications associated with diabetes mellitus such as diabetic retinopathy, thromboembolism disorders such as deep vein or pulmonary thromboembolism. Further exemplary disorders are acute coronary syndrome (ACS), angina, myocardial infarction, cancer, macular degeneration, inflammation, hay fever, atherosclerosis, and/or rheumatoid arthritis.

Exemplary drugs for the treatment and/or prophylaxis of diabetes mellitus or complications associated with diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the term "derivative" refers to any substance, which is sufficiently structurally similar to the original substance so as to have substantially similar functionality or activity (e.g., therapeutic effectiveness).

Exemplary insulin analogues are Gly(A21), Arg(B31), Arg(B32) human insulin (insulin glargine); Lys(B3), Glu (B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Exemplary insulin derivatives are, for example, B29-N-myristoyl-des(B30) human insulin; B29-N-palmitoyl-des (B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-gamma-glutamyl)-des(B30) human insulin; B29-N—(N-lithocholyl-gamma-glutamyl)-des(B30) human insulin; B29-N-(ω-carboxyheptadecanoyl)-des(B30) human insulin and B29-N-(ω-carboxyheptadecanoyl) human insulin. Exemplary GLP-1, GLP-1 analogues and GLP-1 receptor agonists are, for example: Lixisenatide/AVE0010/ZP10/Lyxumia, Exenatide/Exendin-4/Byetta/Bydureon/ITCA 650/AC-2993 (a 39 amino acid peptide which is produced by the salivary glands of the Gila monster), Liraglutide/Victoza, Semaglutide, Taspoglutide, Syncria/Albiglutide, Dulaglutide, rExendin-4, CJC-1134-PC, PB-1023, TTP-054, Langlenatide/HM-11260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, TT-401, BHM-034. MOD-6030, CAM-2036, DA-15864, ARI-2651, ARI-2255, Exenatide-XTEN and Glucagon-Xten.

An exemplary oligonucleotide is, for example: mipomersen/Kynamro, a cholesterol-reducing antisense therapeutic for the treatment of familial hypercholesterolemia.

Exemplary DPP4 inhibitors are Vildagliptin, Sitagliptin, Denagliptin, Saxagliptin, Berberine.

Exemplary hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Exemplary polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20/Synvisc, a sodium hyaluronate.

The term "antibody", as used herein, refers to an immunoglobulin molecule or an antigen-binding portion thereof. Examples of antigen-binding portions of immunoglobulin molecules include F(ab) and F(ab')2 fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region.

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful include, for example, Fab fragments, F(ab')2 fragments, scFv (single-chain Fv) fragments, linear antibodies, monospecific or multispecific antibody fragments such as bispecific, trispecific, and multispecific antibodies (e.g., diabodies, triabodies, tetrabodies), minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Exemplary antibodies are anti PCSK-9 mAb (e.g., Alirocumab), anti IL-6 mAb (e.g., Sarilumab), and anti IL-4 mAb (e.g., Dupilumab).

The compounds described herein may be used in pharmaceutical formulations comprising (a) the compound(s) or pharmaceutically acceptable salts thereof, and (b) a pharmaceutically acceptable carrier. The compounds may also be used in pharmaceutical formulations that include one or more other active pharmaceutical ingredients or in pharmaceutical formulations in which the present compound or a pharmaceutically acceptable salt thereof is the only active ingredient. Accordingly, the pharmaceutical formulations of the present disclosure encompass any formulation made by admixing a compound described herein and a pharmaceutically acceptable carrier.

Pharmaceutically acceptable salts of any drug described herein are also contemplated for use in drug delivery devices. Pharmaceutically acceptable salts are for example acid addition salts and basic salts. Acid addition salts are e.g. HCl or HBr salts. Basic salts are e.g. salts having a cation selected from an alkali or alkaline earth metal, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are known to those of skill in the arts.

Pharmaceutically acceptable solvates are for example hydrates or alkanolates such as methanolates or ethanolates.

Those of skill in the art will understand that modifications (additions and/or removals) of various components of the APIs, substances, formulations, apparatuses, methods, systems and embodiments described herein may be made without departing from the full scope and spirit of the present invention, which encompass such modifications and any and all equivalents thereof.

The invention claimed is:

1. An injector device for delivering a liquid medicament, the injector device comprising:
   an injector body having a proximal end and a distal end,
   a syringe slidably receivable in the injector body and moveable from a first position to a second position towards the distal end of the injector body,
   a needle holder between the syringe and the distal end of the injector body,
   a needle held in the needle holder, the needle including a distal end extending toward an opening in the distal end of the injector body, and a proximal end extending toward the syringe,
   a syringe biasing member within the injector body configured to bias the syringe into the second position, and
   a needle holder biasing member arranged between the needle holder and a distal end of the syringe, the needle holder biasing member being directly attached to the distal end of the syringe and directly attached to the needle holder, the needle holder biasing member configured to bias the needle holder into an extended position, wherein the syringe is spaced from the needle in the first position and is engaged with the proximal end of the needle in the second position, and wherein the needle holder is slidably mounted in the injector body and moveable from a retracted position to the extended position toward the distal end of the injector body.

2. The injector device according to claim 1, wherein the syringe includes a distal end with an opening sealed with a septum, and wherein the injector device is configured such that the proximal end of the needle pierces the septum when the syringe moves into the second position.

3. The injector device according to claim 1, wherein the injector body includes a needle holder stop against which the needle holder abuts in the extended position.

4. The injector device according to claim 1 wherein the syringe biasing member is configured to exert a greater biasing force than the needle holder biasing member.

5. The injector device according to claim 1, wherein the syringe includes a stopper which is slidable towards the distal end of the syringe to expel medicament therefrom, and wherein the injector device further comprises a stopper biasing member configured to bias the stopper towards the distal end of the syringe.

6. The injector device according to claim 5, wherein the syringe biasing member and the stopper biasing member are coil springs and the stopper biasing member is concentric with, and at least partially received within, the syringe biasing member.

7. The injector device according to claim 5, further comprising a release mechanism configured to retain the stopper against the bias of the stopper biasing member and operable to release the stopper to allow movement within the syringe under the bias of the stopper biasing member.

8. The injector device according to claim 5, wherein a syringe ram includes a hollow section and the stopper biasing member is at least partially received within the hollow section of the syringe ram.

9. The injector device according to claim 1, further comprising a syringe ram in abutment with the syringe and disposed towards the proximal end of the injector body from the syringe, and wherein the syringe biasing member acts on the syringe ram to exert a biasing force on the syringe.

10. The injector device according to claim 1, further comprising an actuation mechanism configured to retain the syringe in the first position until the actuation mechanism is activated and the syringe is released.

11. The injector device according to claim 1, further comprising a needle sleeve moveable between an extended position in which the needle sleeve extends from the distal end of the injector body and surrounds the needle, and a retracted position in which the needle sleeve is retracted into the injector body to expose the needle.

12. The injector device according to claim 1, where the syringe contains a liquid medicament or a cartridge of liquid medicament.

13. A method comprising:
moving a syringe distally within an injector body of an injector device from a first position in which the syringe is spaced from a needle held in the injector body by a needle holder into a second position under a bias of a syringe biasing member,
wherein a needle holder biasing member is arranged between the needle holder and a distal end of the syringe, the needle holder biasing member is directly attached to the distal end of the syringe and directly attached to the needle holder, and the needle holder biasing member is configured to bias the needle holder into an extended position;
wherein the syringe engages a proximal end of the needle in the second position.

14. The method of claim 13, wherein a septum of the syringe is pierced such that medicament within the syringe and the needle are in fluid communication when the syringe is moved into the second position.

15. The method of claim 13, further comprising:
moving a needle sleeve relative to the injector body from a retracted position to an extended position and locking the needle sleeve in the extended position.

16. The method of claim 13, further comprising biasing the needle holder away from the syringe by the needle holder biasing member, wherein the needle holder biasing member connects the needle holder to the syringe.

17. The method of claim 13, further comprising sliding a stopper within the syringe towards the distal end of the syringe to expel medicament from the syringe.

18. The method of claim 13, further comprising retaining the syringe in the first position until an actuation mechanism is activated and the syringe is thereby released.

* * * * *